United States Patent [19]

Shea

[11] Patent Number: 4,802,852
[45] Date of Patent: Feb. 7, 1989

[54] IRRIGATED DRILL AND QUICK-RELEASE CHUCK ASSEMBLY

[75] Inventor: John J. Shea, Memphis, Tenn.

[73] Assignee: Richards Medical Company, Memphis, Tenn.

[21] Appl. No.: 917,669

[22] Filed: Oct. 10, 1986

[51] Int. Cl.⁴ .............................................. A61C 1/14
[52] U.S. Cl. .................................. 433/127; 433/104; 433/128
[58] Field of Search ............... 433/126, 147, 103, 104, 433/114, 84, 85, 131, 128, 127, 146, 147; 279/22; 310/60, 61

[56] References Cited

U.S. PATENT DOCUMENTS

| | | | |
|---|---|---|---|
| 233,709 | 10/1880 | Starr | 433/114 |
| 2,536,017 | 1/1951 | Bamberger | 433/114 |
| 3,631,597 | 1/1972 | Lieb et al. | 433/114 |
| 4,184,256 | 1/1980 | Loge et al. | 433/104 |
| 4,568,283 | 2/1986 | Hotta et al. | 433/104 |

*Primary Examiner*—John J. Wilson
*Attorney, Agent, or Firm*—Nies, Webner, Kurz & Bergert

[57] ABSTRACT

An electric motor-driven drill has an irrigating tube for squirting water onto a drill bur. The tube has convolutions surrounding the motor for cooling the motor and warming the irrigating water. A quick-release chuck holds the bur shank coupled to the motor shaft.

3 Claims, 3 Drawing Sheets

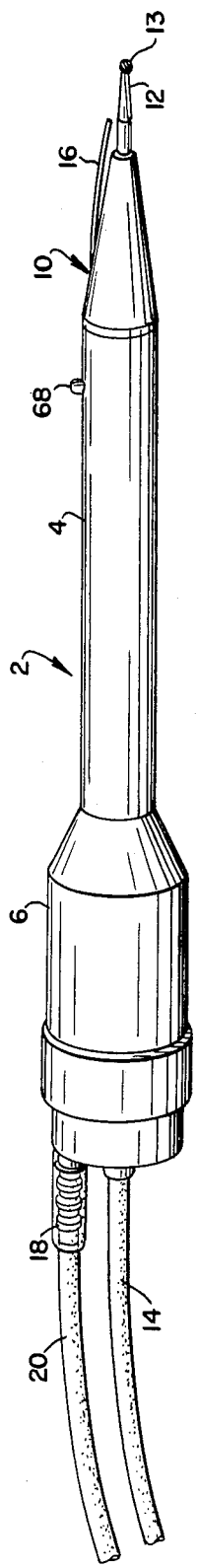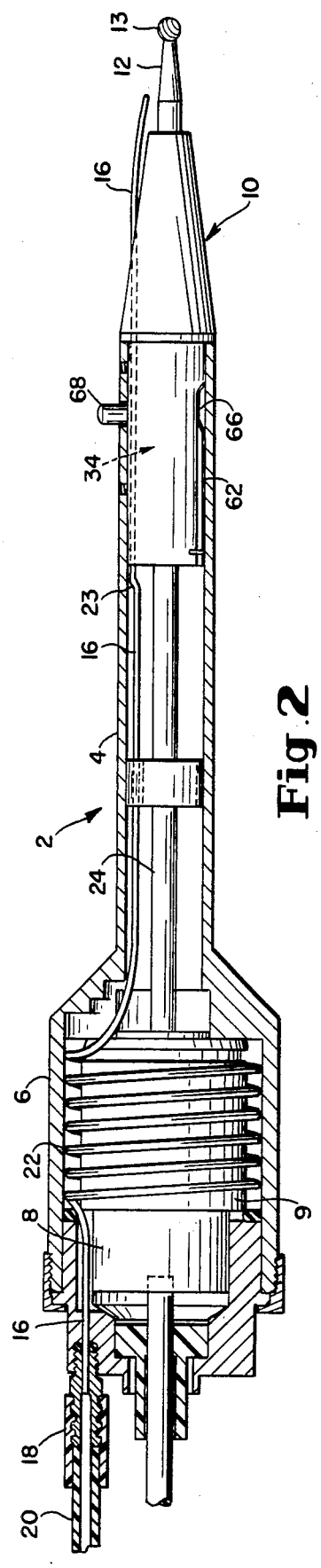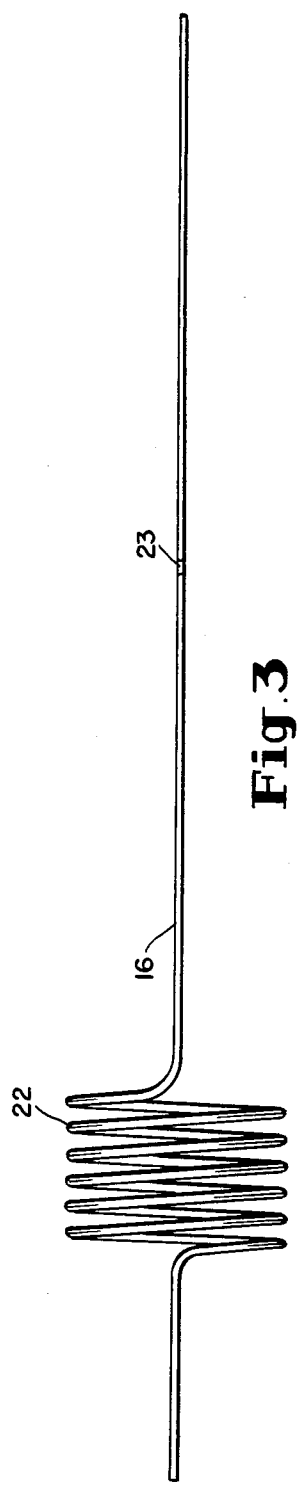

IRRIGATED DRILL AND QUICK-RELEASE CHUCK ASSEMBLY

OBJECTS

The primary object of this invention is to provide a high speed, electric motor driven drill having an irrigation system for squirting water onto a bur while simultaneously cooling the motor, plus a quick-release, quick-engaging chuck assembly for engaging and firmly holding in place a bur shank. The drill of this invention has particular utility in performing certain operations where extremely high speed and vibration-free rotation of a bur is needed and where water is squirted onto the bur so as to irrigate it during its cutting operations. In this latter connection, it is intended to provide an irrigating tube so devised that the water used to irrigate the bur is used for cooling the motor so that not only is the drill protected against heat generated by the driving motor but also that the irrigating water is tempered somewhat as it passes around and extracts heat from the motor.

A further object is to provide a chuck into which a bur shank is drivingly engaged, and which locks the bur shank in so that only minor manipulation, i.e., a slight rotative movement at most is needed to insert the bur shank and which releases the bur shank in response to only a very short pressing-in of a plunger The bur shank used in this chuck has a flat end which drivingly engages in a slot in the motor drive shaft, and near the flat end is a annular groove in this bur shank, into which the inner race of the ball bearing engages so as to block outward movement of the bur shank until the inner race of the ball bearing is removed from its blocking position. By this means, it is intended to provide for only slight movement of the ball bearing between its blocking and unblocking positions, the object here being to require only slight manipulative movements on the part of the operator in order to lock or unlock the bur shank to or from its driving position and to assure that, once the bur shank is locked, it is virtually impossible for it to accidentally become loose or wobbly, which might prove fatal to the patient undergoing certain surgical procedures.

These and other objects will be apparent from the following specification and drawings in which:

FIG. 1 is a perspective view of the drill with the bur installed;

FIG. 2 is a cross sectional view of the casing with the inner part shown in side elevation;

FIG. 3 is a side elevation of the motor cooling and irrigation tube removed from the assembly;

FIG. 4 is a longitudinal cross section of the forward part of the assembly with the bur blocked in;

Figure 4:
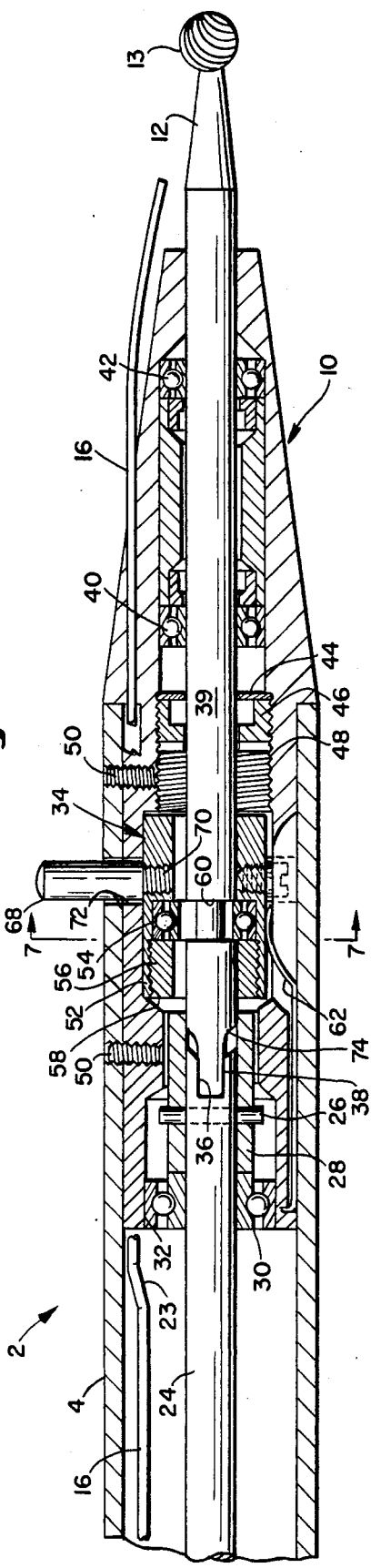

Referring now to the drawings, in which like reference numerals denote similar elements, the drill 2 is enclosed within a housing 4 having an enlargement 6 at its rear end for accommodating a motor 8 having a generally cylindrical outer surface portion 9. At the forward part of the housing is a nose cone 10 from which normally projects the shank 12 of a bur 13. Leading from the rear end of the housing are an electrical supply cord 14 and an irrigation tube 16 which is coupled as 18 to a water supply tube 20. The water supply tube 20 has convolutions 22 which surround the cylindrical outer surface portion and cool the motor when water passes through the irrigation tube. The tube has an off-set 23 so as to permit it to pass around the chuck assembly 34 when it, the tube, is inserted from the rear of the housing.

The motor 8 has a drive shaft 24 which extends forwardly through the hollow interior of housing 4. The forward portion of the drive shaft is connected by a pin 26 to a sleeve 28 which is rotatably supported in the housing by a bearing 30. Bearing 30 is mounted in the rear end of the nose cone by press fit as indicated at 32.

The chuck assembly 34, best shown in FIGS. 4, 5, 7, and 8 is as follows:

In the forward end of drive shaft 24 is a cross slot 36 into which a flat end 38 of bur shank 12 engages. The forward end of the bur shank is rotatably supported in the nose cone by bearings 40 and 42 so that the bur shank rotates about a fixed axis without vibration or rattling. A seal 44 is held in place by a collar 46 threaded as at 48 into the nose cone. If desired, the nose cone may be secured to the housing by one or more set screws 50, although there are other known mechanical means for doing this. At the heart of the chuck assembly is the sleeve 52 which has slight freedom of transverse movement with respect to the bur shank as well as the fixed elements of the housing and its nose cone. Supported in sleeve 52 is a bearing 54 which is held in place by a nut 56 threaded as at 58 into the sleeve. Near the rear of bur shank 12 is an annular groove 60 into which the inner race of bearing 54 may engage so as to block the bur shank 12 against outward movement. Sleeve 52 is biased by leaf springs 62, 64 so that the inner race of bearing 54 normally engages in the annular groove 60 in the bur shank when the groove 60 is brought into registry with the bearing race. As will be seen by comparing FIGS. 4, 5, 7, and 8, sleeve 52 is moved downwardly (as seen in the drawings) by depressing a plunger 68 which is threaded as at 70 in sleeve 52 and freely passes through openings 72 in the housing and nose cone.

Figure 5:
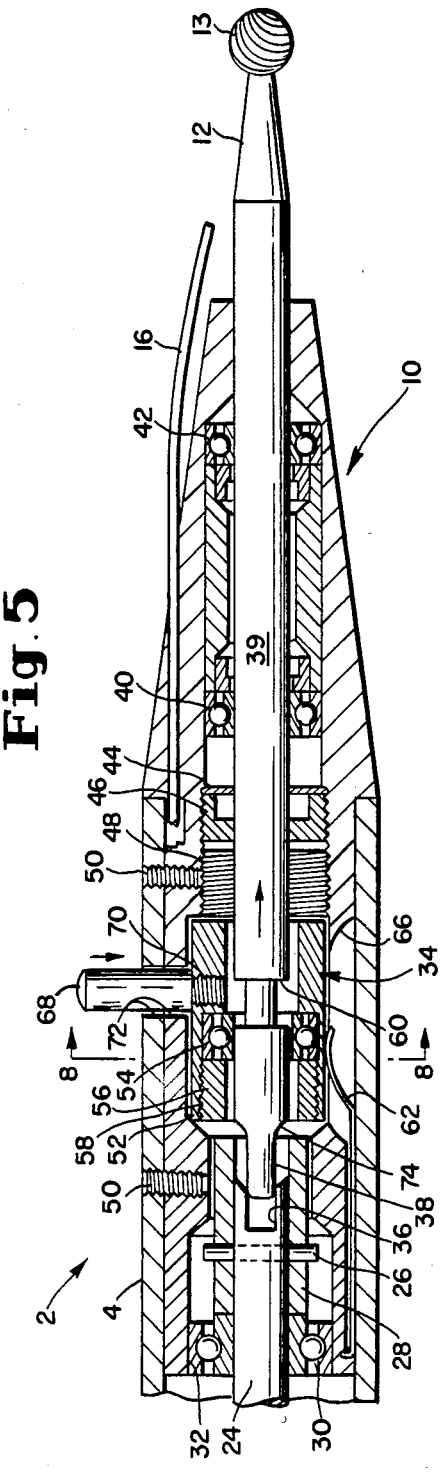
FIG. 5 is a view similar to FIG. 4 but with the bur shank unlocked.
Figure 6:
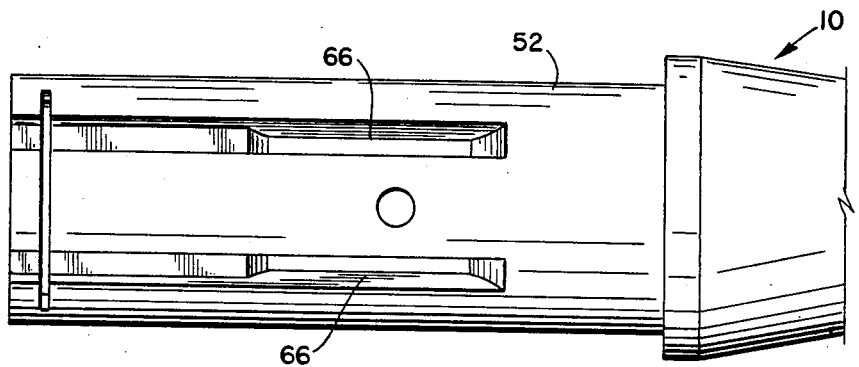
FIG. 6 is a planned view of the inner side of the housing showing the spring-accommodating grooves.
Figure 7:
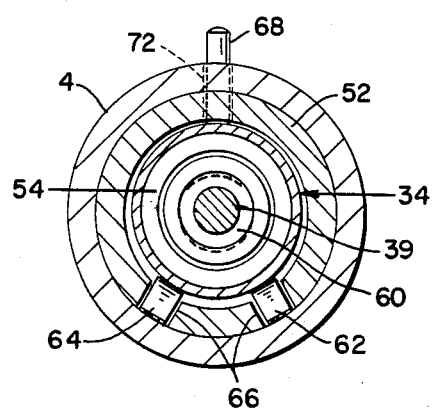
FIG. 7 is a transverse cross section along the line 77 of FIG. 4.
Figure 8:
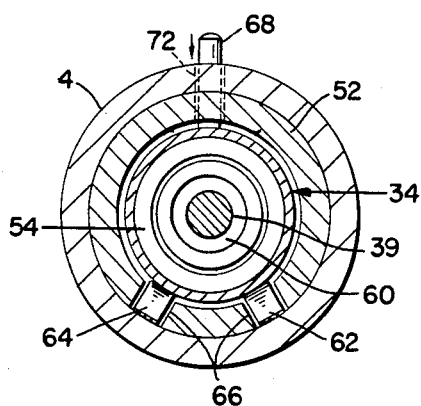
FIG. 8 is a transverse cross section along the line 88 of FIG. 5.

In operation, when the bur shank is inserted into the chuck assembly, the tapered shoulder 74 at the inner ends of the flats permit the bur shank to crowd its way to the inner race of bearing 54 and move into place, as seen in FIG. 4, with slight rotary manipulation, if needed, to bring the flat end of the bur shank into registry with the cross slot 36 in the end of the motor drive shaft. As soon as the annular groove 60 moves into registry with the inner race of bearing 54, leaf springs 62, 64 force sleeve 52 towards bur shank 12 so that the bearing 52 snaps in place into annular groove 60, thereby blocking outward movement of the bur shank. When it is desired to remove the bur, plunger 68 is depressed so as to move sleeve 52 downwardly, as seen in FIGS. 4 and 5, thereby clearing the bearing 54 from the annular groove 60. This permits the bur to be removed. It should be noted that only slight depression of plunger 68 is needed to move the bearing 54 from its blocking position (FIG. 4) to its unblocking position (FIG. 5).

I claim:

1. A drill comprising an elongate hollow casing defining a nose portion at a front end thereof and an electric motor in the other end,
   a bur having an elongate shank with opposite flats on a free end thereof and an annular groove spaced from said flats,
   bearing means in said nose portion for rotatably supporting the bur shank,
   said motor having a drive shaft with a slotted end for accommodating the flatted end of the bur shank for rotatably driving the bur,
   and a chuck for releasably holding the bur shank in the slotted end of the motor shaft,
   said chuck comprising annular bearing means and a sleeve engaged around the bearing,
   the bearing means closely surrounding the bur shank and being engageable into the annular groove,
   said sleeve having limited freedom to move transversely of the length of the bur shank, the bearing means being moveable inwardly into the groove to thereby block outward movement of the bur shank from the slotted end of the motor drive shaft and being moveable outwardly of the groove to thereby unblock the bur shank,
   spring means engaged between the casing and the sleeve whereby to bias the same so as to cause said bearing means to move inwardly into the groove,
   and a manually operable plunger having one end attached to the sleeve and the other end extending outwardly of the casing whereby, upon pressing said plunger inwardly the bearing race is caused to move outwardly of the groove.

2. A drill as claimed in claim 1, said spring means comprising of at least one leaf spring having one end portion engaged in a slot in the inner side of the housing and an opposite end engaged against said sleeve.

3. A drill as claimed in claim 2, said bearing means comprising a ball bearing having outer and inner races, said outer race being engaged in said sleeve, said inner race being engageable into said annular groove in said bearing shank.

* * * * *